United States Patent [19]

Negus et al.

[11] Patent Number: 5,591,161

[45] Date of Patent: Jan. 7, 1997

[54] ANGLED BEAM DELIVERY HANDPIECE FOR LASER OR OTHER MONOCHROMATIC LIGHT SOURCE

[75] Inventors: Charles C. Negus; Stephen J. Linhares, both of Taunton, Mass.

[73] Assignee: PLC Medical Systems, Inc., Milford, Mass.

[21] Appl. No.: 548,269

[22] Filed: Oct. 25, 1995

[51] Int. Cl.⁶ .................................................. A61B 17/36
[52] U.S. Cl. ......................................................... 606/17
[58] Field of Search ........................ 606/4, 5, 6, 10, 606/11, 12, 13, 14, 15, 16, 17, 19

[56] References Cited

U.S. PATENT DOCUMENTS

| | | | |
|---|---|---|---|
| 4,760,840 | 8/1988 | Fournier Jr. et al. | 606/15 |
| 4,849,859 | 7/1989 | Nagasawa | 606/17 |
| 4,955,882 | 9/1990 | Hakky | 606/14 |
| 4,963,142 | 10/1990 | Loerstcher | 606/6 |
| 5,112,328 | 5/1992 | Taboada et al. | 606/19 |
| 5,190,536 | 3/1993 | Wood et al. | 606/17 |
| 5,261,904 | 11/1993 | Baker et al. | 606/17 |
| 5,288,288 | 2/1994 | Lewis et al. | 606/14 |
| 5,300,066 | 4/1994 | Manoukian et al. | 606/17 |
| 5,312,398 | 5/1994 | Hobart et al. | 606/17 |
| 5,336,215 | 8/1994 | Hsueh et al. | 606/17 |
| 5,342,352 | 8/1994 | Franken et al. | 606/19 |
| 5,352,221 | 10/1994 | Fumich | 606/17 |
| 5,496,309 | 3/1996 | Saadat et al. | 606/15 |

FOREIGN PATENT DOCUMENTS 2826383  12/1979  Germany .................................. 606/15

Primary Examiner—Angela D. Sykes
Assistant Examiner—Sonya Harris-Ogugua
Attorney, Agent, or Firm—Iandiorio & Teska

[57] ABSTRACT

An angled beam-delivery handpiece includes a barrel for delivering a monochromatic light beam; a contact surface at the distal end of the barrel; a window in the side of the barrel proximate the contact surface; an aperture in the contact surface; and a refractive element in the barrel above the window for diverting the beam carried by the barrel to exit the aperture at an angle to the laser beam in the barrel.

8 Claims, 4 Drawing Sheets

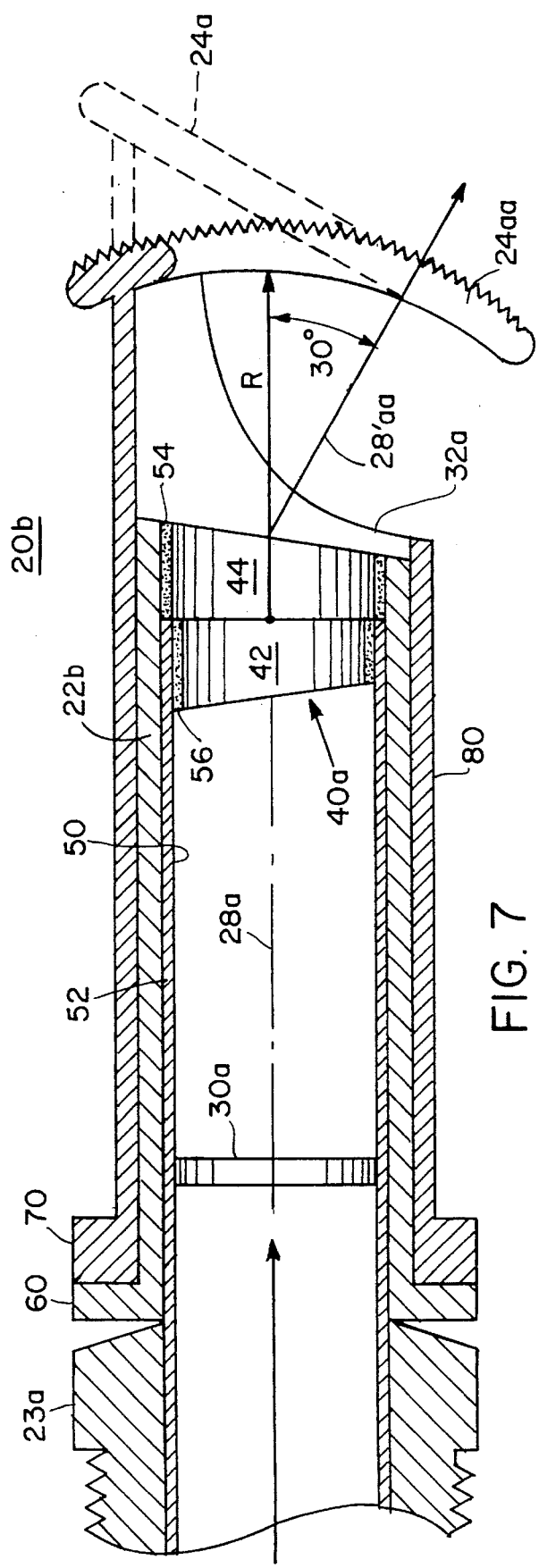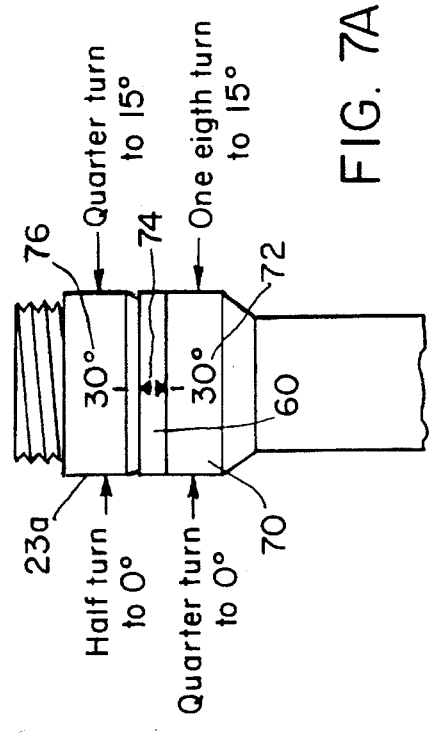

5,591,161

ANGLED BEAM DELIVERY HANDPIECE FOR LASER OR OTHER MONOCHROMATIC LIGHT SOURCE

FIELD OF INVENTION

This invention relates to an angled beam delivery handpiece for a laser or other monochromatic light source, and more particularly to such a handpiece for diverting a laser beam in a surgical laser.

BACKGROUND OF INVENTION

In laser surgery, such as transmyocardial revascularization, it is often desirable to have the laser beam exit the handpiece at some angle other than 0°, for example, 15°, 20°, 30°, 45°, 90°. Redirection or diversion of the laser beam at 90° or thereabouts can be achieved with a mirror but as the diversion angle diminishes the mirror required becomes larger and larger to accommodate the incident area of the beam. This necessitates a larger and larger mirror or reflector in the lengthwise direction, i.e., along the laser beam direction which results in the mirror coming close or even touching the heart wall or other part of the patient to be serviced. That subjects the mirror to greater potential of contamination from body fluids and the ablative exhaust from the laser-struck heart tissue or other tissue.

SUMMARY OF INVENTION

It is therefore an object of this invention to provide an improved angled beam delivery handpiece for a laser such as a surgical laser or other monochromatic light source.

It is a further object of this invention to provide such an improved angled beam delivery handpiece which is compact and eliminates the need for elongated reflecting means.

It is a further object of this invention to provide such an improved angled beam delivery handpiece which is adjustable over a range of beam delivery angles.

It is a further object of this invention to provide such an improved angled beam delivery handpiece which can divert both the surgical laser beam and a second beam of different wavelength but converge them on the same target area.

It is a further object of this invention to provide such an improved angled delivery handpiece which avoids close proximity of the diverting optics to the heart or other body parts.

The invention results from the realization that a simple, rugged handpiece for delivery of a diverted laser beam or other monochromatic beam can be achieved without enlarged, angled mirrors by using a refractive element to divert the beam to the desired angle.

This invention features an angled beam-delivery handpiece. There is a barrel for delivering a monochromatic light beam, a contact surface at the distal end of the barrel, a window in the side of the barrel proximate the contact surface, an aperture in the contact surface. A refractive element in the barrel above the window diverts the beam carried by the barrel to exit the aperture at an angle to the laser beam in the barrel.

In a preferred embodiment the contact surface may be perpendicular to the diverted beam. The contact surface may be "U" shaped, the aperture may open on one side and the contact surface may be elongated, being substantially the same width as the barrel in the direction across the "U" shape and longer than the barrel width in the transverse direction. The refractive element may include an optical prism and the optical prism may include two relatively rotatable sections for varying the diversion angle of the beam. The optical prism may also include a dichroic prism for diverting the beam and a second beam of different wavelength to the same target area.

DISCLOSURE OF PREFERRED EMBODIMENT

Other objects, features and advantages will occur to those skilled in the art from the following description of a preferred embodiment and the accompanying drawings, in which:

FIG. 7 is a cross-sectional schematic diagram of a portion of a handpiece showing the mechanism for rotating the two prism sections relative to one another;

FIG. 7A is an enlarged more detailed view of the gripping ring and associated assembly of FIG. 7;

Figure 1:
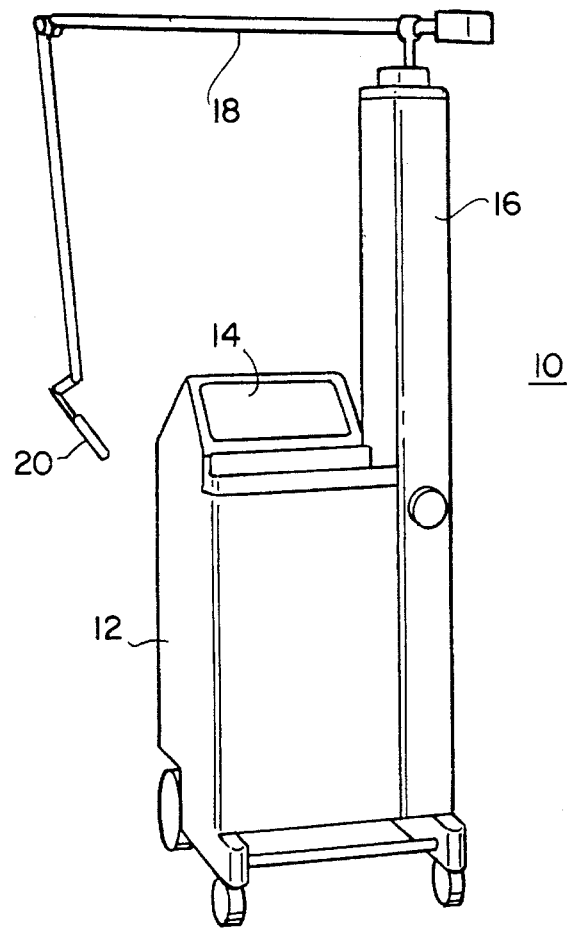
FIG. 1 is a three-dimensional view of a laser system which utilizes the handpiece of this invention.
Figure 2:
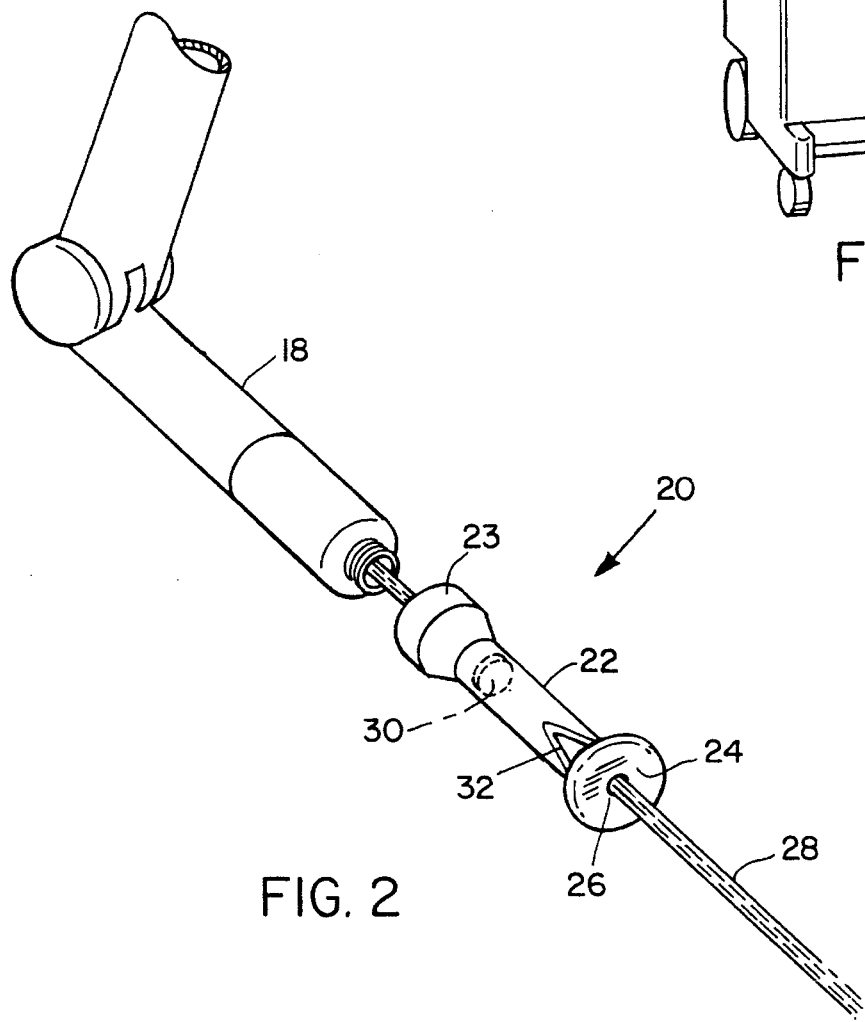
FIG. 2 is an enlarged, more detailed, exploded three-dimensional view of a portion of the articulated arm in FIG. 1 and a conventional handpiece.

There is shown in FIG. 1 a surgical laser system 10 which includes a power supply and control 12 operated through control and monitor screen 14 to operate laser 16. The output from laser 16 is directed through articulated arm 18 to handpiece 20 typically held by the operator or surgeon to direct the beam at the desired target. Handpiece 20 includes an enlarged threaded portion 23 for connection to articulated arm and a barrel 22 at the end of which is contact surface 24 which for example contacts the heart of the patient on which transmyocardial revascularization is being performed. There is an aperture 26 in contact surface 24 through which beam 28 exits to strike the heart. A lens 30, shown in phantom, in barrel 22 focuses laser beam 28 at a predetermined distance typically at the contact surface 22. Barrel 22 also includes a side window 32 through which the user can view the beam as it enters aperture 26. Window 32 also acts as a venting hole for the ablative plume which rises from the heart or other tissue struck by the laser beam 28.

Figure 3:
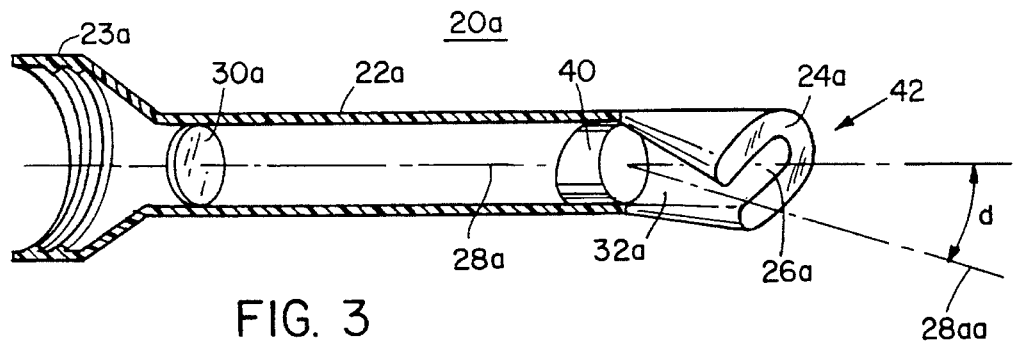
FIG. 3 is a three-dimensional partially sectional diagrammatic view of a handpiece according to this invention.
Figure 4:
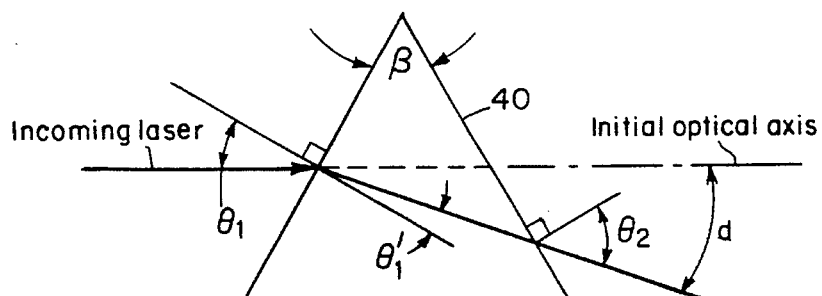
FIG. 4 is a schematic ray diagram showing the parameters considered in the refractive element used to divert the beam in the handpiece of FIG. 3.

In accordance with this invention handpiece 20a, FIG. 3, includes barrel 22a which includes a similar connection portion 23a and lens 30a. However, in the lower portion of the barrel just above window 32a is prism 40 which diverts laser beam 28a resulting in the diverted beam 28aa which exits through aperture 26a in contact surface 24a. In this particular embodiment aperture 26a is open at one end 42 and contact surface 24a is formed in the shape of a "U". Specifically, contact surface 24a is approximately the same width as the barrel in the direction across the legs of the "U" and is elongated in the orthogonal direction in order to facilitate its insertion between human ribs without undue spreading of the fibs. The particular angle of diversion d is determined, among other things, by the angle of the prism, β, and the index of refraction of the material from which the prism is made. For example, for a diversion angle d of 30° in FIG. 3, the β angle of prism 40 would be 18° if the material were zinc selenide having a refractive index of 2.403 and the laser beam were a $CO_2$ laser beam having a wavelength 10.6μ. The prism can be designed beginning with the expression $$d = \theta_1 + \theta_2 - \beta \quad (1)$$

where d is the diversion angle, $\theta_1$ is the angle that the incoming laser beam, $\theta_1$, FIG. 4, makes with the normal to the surface of the prism, and $\theta_2$ is the angle that the diverting laser beam makes with the normal to the exiting surface. $\theta'_1$ is the diversion angle of the laser beam leaving the first face internal to the prism and normal to the entrance surface. $\theta_2$ is then calculated according to the expression $$\theta_2 = \sin^{-1}[n\sin(\beta - \theta_1')] \quad (2)$$

$\theta'_1$ is calculated according to the expression $$\theta'_1 = \sin^{-1}\left(\frac{1}{n}\sin\theta_1\right) \quad (3)$$

and the index of refraction in this case is 2.403 for zinc selenide.

Figure 5:
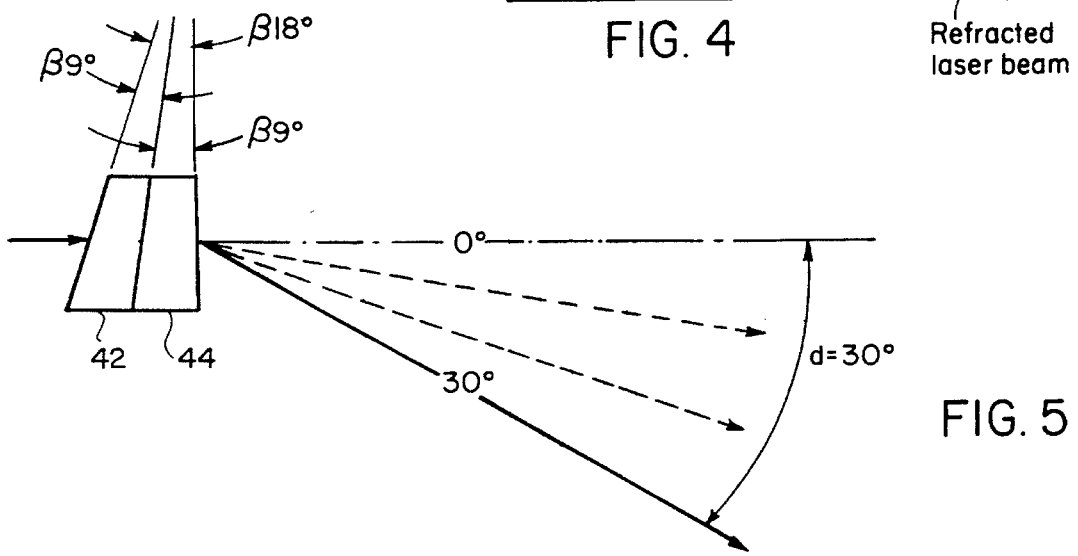
FIG. 5 is schematic diagram of a prism similar to that shown in FIGS. 3 and 4 having two mutually rotatable sections for varying the diversion angle of the beam.
Figure 6:
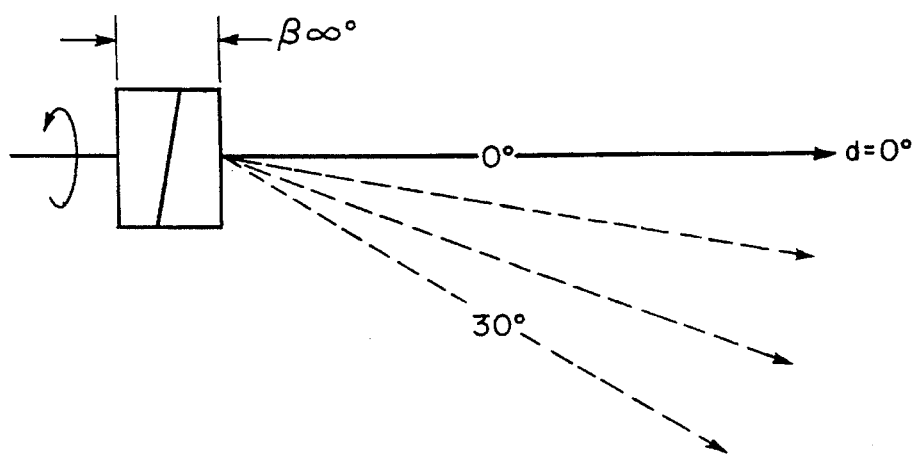
FIG. 6 is schematic diagram of the two prisms shown fully rotated 180° out of phase where the beam diversion is zero.

If it is desired to be able to vary the range of the diversion angle so that the operator for example can divert the laser beam from zero to 30° at his election, the prism can be divided into two sections. For example, prism 40a, FIG. 5, could be divided into two sections 42 and 44 each having a β of 9°. Then when the two sections 42 and 44 are rotated relative to one another the diversion angle d will vary between zero and 30°. When the two prisms are aligned as shown in FIG. 5, the diversion angle d is 30°. When they are totally out of phase with one another, as shown in FIG. 6, then the diversion angle will be zero.

The relative rotation between prism sections 42 and 44 can be accomplished with the mechanism shown in FIG. 7, where it is shown that barrel 22b of handpiece 20b includes internal bore 50 that receives a rotatable inner tube 52. Prism section 44 is attached by adhesive 54 to barrel 22b; prism section 42 is attached by adhesive 56 to the inner tube 52 that is rotatable with respect to barrel 22b. The position of the undiverted beam 28aa at 0° is shown in phantom line while the beam diverted to the full 30° is shown at 28'aa. Also shown in FIG. 7 is the contact surface 26a disposed at an angle to the original laser beam 28a and generally normal to the maximally diverted exiting beam at 30°. Although prism 40 is shown divided into two equal portions 42 and 44, this is not a necessary limitation of the invention. The sections may be unequal so that instead of 50% each they are divided 60%–40%, 70%–30%, or any other ratio. However, when the sections are not equally divided the full range of 0°–30° will not be obtained; the range will be diminished in accordance with the ratio. Although the example in this embodiment is of a 30° maximum diversion of the beam this is not a necessary limitation of the invention as the prism can be calculated for any desired angle of diversion, taking into account the wavelength and index of refraction requirement. A gripping ting 60 on the outside of barrel 22b can be gripped by the user to rotate barrel 22b relative to inner tube 52 which is fixedly attached to the threaded connection portion 23a of handpiece 20b.

The counter-rotation of the two prisms will divert the optical path of the transmitted beam in an arc, so that the focal point will travel in a radius "R", FIG. 7, from approximately the center of the two prisms. The contact surface then must also be curved about this radius to provide a surface that will be normal to the target tissue.

The contact surface will have to remain fixed, relative to the counter-rotating prisms, so that each degree of rotation of one prism in relation to the contact surface is matched by the opposing prism rotation in the opposite direction. This can be accomplished in FIG. 7 by connecting the contact surface 24aa to an outer tube 80 which can rotate about the middle tube 22b, and terminates in another gripping ring 70.

The alignment of the three components (two prisms and contact surface) can then be accomplished by aligning degree indications 72 and 76 on the outside surface of the respective gripping rings 23a and 70, FIG. 7A, with alignment mark 74 on gripping ring 60. Quarter turns of ring 23a would then compare with ⅛ turns of ring 70 in the same direction, relative to 60.

Figure 8:
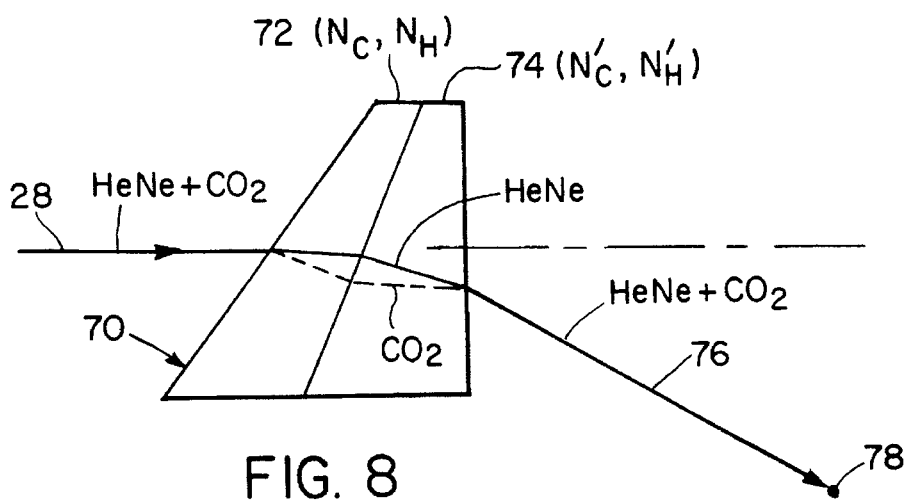
FIG. 8 is a schematic ray diagram of a dichroic prism which diverts two beams of two different wavelengths but converges them on the same target.

In some applications it is necessary to accommodate two laser beams or monochromatic beams of different wavelengths, divert both of them by the same amount and have them strike the same target area. For example, in one $CO_2$ surgical laser there is accompanying it a helium neon laser (HeNe) which provides a red light that can be easily seen to aim the device before the $CO_2$ beam is energized. To accomplish this double diversion a dichroic prism 70, FIG. 8, may be used. Prism 70 would thus have two sections, 72 and 74 which are fixed with respect to one another but have different indexes of refraction for the $CO_2$ and HeNe laser beam wavelengths. For example, prism section 72 would have a first index of refraction $N_c$ for the $CO_2$ wavelength and a different index of refraction $N_H$ for the HeNe wavelength, while the second prism section 74 would have an index of refraction $N'_c$ for the $CO_2$ wavelength which would differ from the index of refraction of that wavelength $N_c$ in prism 72. Likewise index of refraction $N'_H$ of prism 74 would differ from the index of refraction $N_H$ for the HeNe laser wavelength in prism 72. In this way each beam is diverted differently by the desired amount, through each separate element, 72 and 74, and yet they recombine as shown at 76 to strike the same target area 78. This configuration could be accomplished with more than just two elements.

Figure 9:
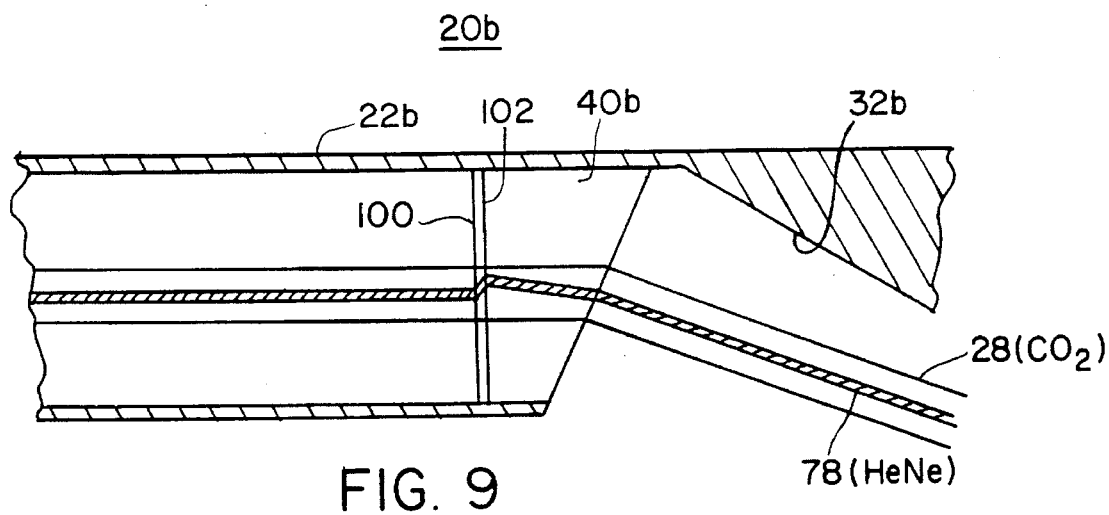
FIG. 9 is a schematic side elevational view of a portion of the handpiece showing an alternative embodiment of the invention using a grating on the prism surface for diverting the HeNe and $CO_2$ beams and converging them on the same target.
Figure 10:
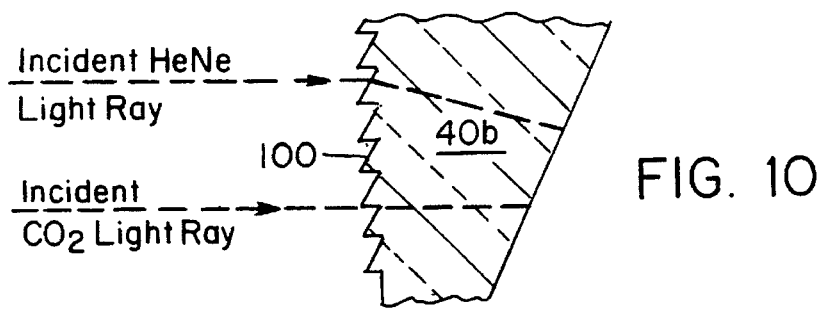
FIG. 10 is an expanded view of the grating of FIG. 9.

In another configuration, the HeNe beam 78 and $CO_2$ beam 28 can be diverted but made to converge on the same target by incorporating an optical grating 100, FIG. 9, on surface 102 of prism 40b so that the grating is transparent to the wavelength of the $CO_2$ laser beam 28 but refracts the wavelength of the HeNe laser beam 78. This results in a matched output refractive angle for both wavelengths and converges them on the same target. Such a grating would be etched or scribed into the surface of the prism, as shown in FIGS. 9 and 10.

Although specific features of this invention are shown in some drawings and not others, this is for convenience only as each feature may be combined with any or all of the other features in accordance with the invention.

Other embodiments will occur to those skilled in the art and are within the following claims:

What is claimed is:

1. An angled beam delivery handpiece comprising:

a barrel for delivering a monochromatic light beam;

an apertured contact surface at the distal end of said barrel for contacting tissue; and a refractive element in said barrel for diverting the beam carried by the barrel to exit said aperture at an angle relative to the laser beam in said barrel.

2. The handpiece of claim 1 in which said refractive element includes two sections, said handpiece further including means for rotating one section relative to the other for varying the diversion angle of said beam.

3. The handpiece of claim 2 in which said means for rotating includes a rotatable tube within said barrel, one of said sections affixed to said rotatable tube.

4. The handpiece of claim 2 in which said contact surface is disposed at an angle relative to the laser beam in said barrel.

5. The handpiece of claim 4 further including means for rotating said contact surface.

6. The handpiece of claim 1 in which said contact surface is "U" shaped.

7. The handpiece of claim 6 in which said contact surface is elongated, being substantially the same width as the barrel in the direction across the "U" shape and longer than said barrel width in the transverse direction.

8. The handpiece of claim 1 in which said refractive element includes a dichroic prism for diverting the beam and a second beam of a different wavelength to the same target area.

* * * * *